United States Patent [19]

Ritter et al.

[11] 4,075,320

[45] Feb. 21, 1978

[54] ATTRACTANT FOR ANTS

[75] Inventors: Fridolin Jacob Ritter, Waddinxveen; Friedrich Stein, Schipluiden, both of Netherlands

[73] Assignee: Nederlandse Organisatie voor Toegepast-Natuurwetenschappelijk Onderzoek ten behoeve van Nijverheid, Handel en Verkeer, The Hague, Netherlands

[21] Appl. No.: 592,085

[22] Filed: June 30, 1975

[30] Foreign Application Priority Data

June 28, 1974 Netherlands .......................... 7408757

[51] Int. Cl.$^2$ ............................................ A01N 17/14
[52] U.S. Cl. ..................... 424/84; 424/267; 424/274; 260/326.5 R; 260/326.8; 260/293.53
[58] Field of Search .................. 424/84, 274, 267; 260/326.8

[56] References Cited

U.S. PATENT DOCUMENTS 3,228,957   1/1966   Fremery .......................... 260/326.8

OTHER PUBLICATIONS

Chemical Abstracts, vol. 79 (1973), p. 40136m.

*Primary Examiner*—V. D. Turner
*Attorney, Agent, or Firm*—Brumbaugh, Graves, Donohue & Raymond

[57] ABSTRACT

As a powerful attractant and trail-following substance for ants of the type of the Pharaoh's ant (Monomorium Pharaonis L) which is active in amounts of between $10^{-11}$ and $10^{-5}$ grams has been shown to be 2-(5'-n-Hexenyl)-5-n-pentylpyrrolidine and a few of the homologues of the 5-pentyl radical. Advantageously it can be combined with the previously proposed compound 5-methyl-3-n-butyl-octahydro-indolizine.

10 Claims, No Drawings

ATTRACTANT FOR ANTS

BACKGROUND OF THE INVENTION

The invention relates to an attractant for ants, in particular for the Pharaoh's ant (Monomorium Pharaonis L), as well as to novel substances applied in this attractant and active as attractant and trail-following compound and to methods for the preparation of these novel substances.

The use of agents to attract insects in a condition in which they can be killed or made innoxious, is known in the art. So, for instance, insects can be lured to a certain place with the aid of the attractive agent and there be brought into contact with an insecticide, an insect hormone or an insect pathogen. In this way it is not necessary to spray a pesticide excessively and indiscriminately over large areas, but the combination of pesticide and attractant can be brought as a mixture or by the side of each other on or near the places that have to be protected against the noxious influence of the insects. The attractant can, for instance, also be used in a way known in the art in combination with a trap, enabling one to kill the insects in the trap or stick them onto an adhesive provided on one of the walls of the trap.

An other important application of attractants is signalling the presence, the distribution and the population of the insect. As a result, the presence of the insects can be discovered in time, so that the necessary measures for combating the pest can be taken and it is not necessary to use an insecticide outside the periods of presence of the insects. Moreover, with an attractant a much better picture can be obtained of the extent and the intensity of an insect pest, enabling a more accurate determination and focus of the measures to be taken to combat it.

Ants, of the type of the Pharaoh's ant, in many places form a danger for public health and mostly are extremely difficult to combat. In particular, in buildings with central heating, in bakeries and laundries, but also in private houses they are a great problem. The Pharaoh's ant is an important factor of pathogenous microorganisms for man in many hospitals (see, for instance, Susan H. Beatson, The Lancet, 19th Feb. 1972, page 425). In such places, where the use of toxic substances ought to be avoided as much as possible, attractants are of great importance as a combating means.

In applicant's pending U.S. patent application Ser. No. 459,358, now abandoned in favor of continuation application Ser. No. 646,611 a new powerful attractive agent for ants, such as the Pharaoh's ant (MONOMORIUM PHARAONIS L) has been described, viz. the 5-methyl-3-n-butyl-octahydroindolizine.

SUMMARY OF THE INVENTION

Now a further very powerful new attactive agent for ants was found, in particular for the Pharaoh's ant, the compound 2-(5'-n-hexenyl)-5-n-pentylpyrrolidine, having formula

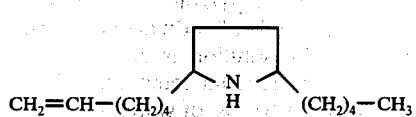 (I)

and a few of its homologues or more specifically of

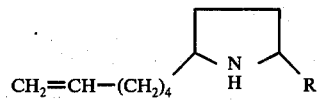 (Ia)

, wherein R represents an alkyl radical having at most 13 carbon atoms, but preferably represents an n-pentyl radical and advantageously also represents an n-heptyl and/or an n-nonyl radical.

DESCRIPTION OF EFFECTS

The said compound was found to be not only an attractive agent for ants, such as the Pharaoh's ant, but also a trail-following compound for the animals. If slowly acting insecticides, insect hormones or insect pathogens are present at the end of a trail of compound (I) or somewhere on this trail, the ants can still return to the place where they came from (their nest) and in so doing leave a trail of compound (I), along which other ants preferably will go and so will be led to the place where the substance toxic to the insects is situated. As a result, the compound according to the invention for checking and controlling the ant pest is of great value.

In particular of importance for an effective combating of an ant pest is the possibility to lure queens with the compound according to the invention, since if the queens are killed further multiplication is prevented. However, luring worker ants is also of importance, because, when most of the worker ants will have been attracted from the nests, the nutritional supply of the nests is stagnated and the larvae and queens still present will starve to death. The workers may also be contaminated with the pesticide and on return drag this to the nest, so that the insects present in the nest that take care of the propagation (queens and male animals), larvae, nymphs and eggs will be extirpated more directly. These methods are in particular of great importance for ants, of the type of the Pharaoh's ant, to make a selective and efficient action possible in case of a pest, when nests are difficult to find as is often the case with this type of ants.

Since the compound according to the invention is already active as attractive agent trail-following compound is extremely slight quantities, is it advisable to apply compound (I) and a few percent of its said homologues as an attractant in combination with a liquid or solid carrier. As a carrier material all compounds known in the art as such for use in insecticides and insect attractants can be applied. The attractive agent can also be applied in or on a sticky surface, on to which the ants remain stuck and can be killed. An other form of application, also known in the art as such is placing the compound according to the invention into a closed container, having walls which are permeable to the vapour of compound (I).

Frequently, in the attractant that contains the compound according to the invention as an active attractive agent, also a poison for the ants will be incorporated. The attractive agent can also be applied for raising the activity of a bait that contains foodstuff for the animals, such as products containing protein (liver), sugar, honey, and the like. Attractants preferred in particular will contain besides compound (I) as an attractive agent also an amount of the compound mentioned above, described in Applicant's previous Patent Application, 5-methyl-3-n-butyl-octahydroindolizine, so that a synergistic effect is obtained.

REACTION SCHEMES

The compound, having formula (I), can be prepared according to various synthetic methods, reactions being applied which are known per se for the synthesis of related compounds. A method that is particularly preferred is that which is started from compound 5-n-pentylpyrolidon-2 known as such and having formula (II). By reaction with 6-heptenoyl chloride, formula (III) from the former, the new compound N-(6'-heptenoyl)-5-n-pentylpyrrolidon-2 is obtained (formula (IV) ). The latter compound then by heating with, for instance, calcium oxide is converted into 2-(5'-n-hexenyl)-5-n-pentyl-1-pyrroline, having formula (V) which likewise, is a new compound.

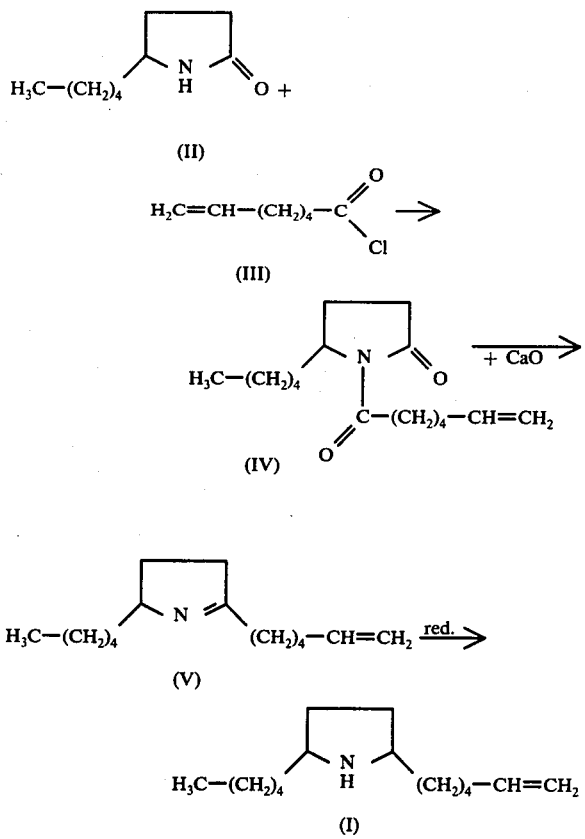

From this then compound (I) is obtained by selective reduction of the N=C bond. A suitable reducing agent for this is, for instance, sodium borohydride, but other reducing agents can also be used.

According to another suitable method of preparation 5-n-pentylpyrrolidon-2 is also started from, which is converted with an alkylating agent, for example trialkyloxoniumfluoroborate (alkyl is methyl or ethyl) into 2-alkoxy-5-n-pentyl-1-pyrroline (VI). By reaction with 5-n-hexenylmagnesium bromide (VII), from this 2-(5'-n-hexenyl)-5-n-pentyl-1-pyrroline is obtained, which then is reduced in the way mentioned above with, for instance, NaBH$_4$ into compound (I).

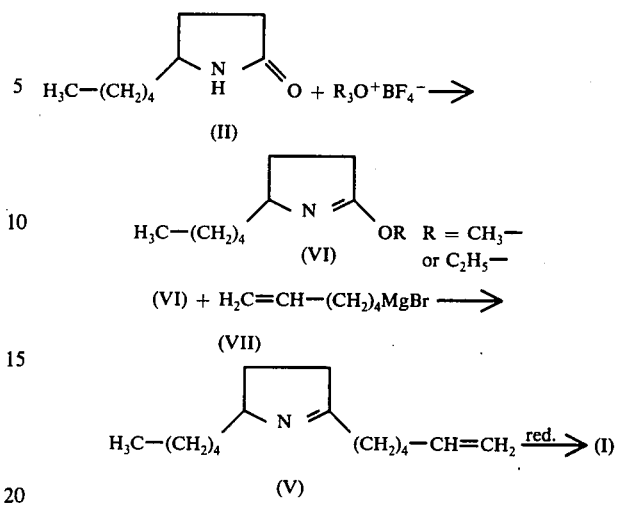

However, as already stated before, compound (I) can also be prepared according to various other synthetic methods known per se in the art. The corresponding n-heptyl and n-nonyl compounds can be prepared correspondingly e.g. by starting from 5-n-heptylpyrrolidon-2 of 5-n-nonylpyrrolidon-2 respectively.

COMPARATIVE EXAMPLES

Example I

Preparation of 2-(5'-n-hexenyl)-5-n-pentylpyrrolidine (a) To a well-stirred solution of 155 gms. (1 mol) 5-n-pentylpyrrolidon-2 in 1.5 ls. of toluene at 118° C in a period of time of 15 minutes 161 gms. (1.1 mol) of 6-heptenoyl chloride is added dropwise, whereupon the reaction mixture is still kept at 118° C for 24 hours. After cooling down of the reaction mixture 400 mls. of water are added, whereupon the organic layer is separated, rinsed out with 2 × 25 mls of a 10% sodiumbicarbonate solution and 1 × 25 ml of water and next dried over sodium sulphate. After removing the solvent the residue is distilled, 236 gms of N-(6'-heptenoyl)-5-n-pentylpyrrolidon-2 being obtained (yield 89% calculated on 5-n-pentylpyrrolidon-2). Boiling-point: 125°-128° C at 0.002 mm Hg; n$_D^{20}$ : 1.4790. The NMR spectrum, infra-red spectrum and mass spectrum are in accordance with the structure indicated.

(b) A mixture of 10 gms. (38 mmol) of N-(6'-heptenoyl)-5-n-pentylpyrrolidon-2 and 8 gms. (140 mmol) of calcium oxide are heated in a small retort for 5 minutes at 290°-300° C by means of a liquid metal bath. Immediately following this (within approx. 5 minutes), the reaction product formed is distilled under atmospheric pressure and the crude product thus obtained is further purified by means of fractional distillation under reduced pressure. In this way 3.0 gms. of 2-(5'-n-hexenyl)-5-n-pentyl-1-pyrroline are obtained (yield 36%) with a boiling-point of 70° C at 0.08 mm Hg; n$_D^{20}$ : 1.4648. The NMR, infra-red and mass spectra are in accordance with the structure expected.

(c) To a solution of 10 gms (45 mmol) of 2-(5'-n-hexenyl)-5-n-pentyl-1-pentyl-1-pyrroline in 100 mls. of methanol 0.849 (22 mmol) of sodium borohydride are added, whereupon the solution is stirred at ambient temperature for 24 hours. After removal of the solvent under reduced pressure 10 mls. of water are added so as to dissolve the excess of sodium borohydride. The product formed is taken up in 100 mls. of ether. After drying of this layer of ether and removal of the solvent 2-(5'-n-hexenyl)-5-n-pentylpyrrolidine is obtained in a quantitative yield as a light brown coloured product. From this by distillation a colourless substance is obtained, having a boiling point of 80° C at 0.08 mm Hg; $n_D^{20}$: 1.4625. The NMR, infra-red and mass spectra are in correspondence with the structure assumed.

EXAMPLE II

Preparation of 2-(5'-n-hexenyl)-5-n-pentyl-1-pyrroline (a) To a well stirred solution of 10.0 g (0.05 mol) of triethyloxoniumfluoroborate in 26 ml of anhydrous methylene chloride at 5°–10° C, 8,1 gms. (0.052 mol) 5-n-pentylpyrrolidon-2 are added. After 18 hours 7,3 gms. 50% potassium carbonate solution are added at 0° C. The solid potassium fluoroborate is removed by filtration. After removal of the solvent, the residue is distilled off, 6.4 gms. of 2-ethoxy-5-n-pentyl-1-pyrroline being obtained. Boiling point: 59° C (0.05 mm Hg); $n_D^{20}$ : 1.4474 (yield: 67%, calculated on 5-n-pentylpyrrolidon-2).

(b) A solution of 32.6 gms. (0.2 mol) of 5-n-hexenyl-magnesium-bromide in 300 mls. of ether is mixed with 300 mls. of dry benzene, whereupon the greatest part of the ether is distilled off. To the remaining solution is added dropwise 32.9 gms. (0.18 mol) of 2-ethoxy-5-n-pentyl-1-pyrroline, whereupon the solution is heated on a water bath for 8 hours. Upon cooling the reaction mixture is decomposed with 100 mls. of water, whereupon the organic layer is separated and the water layer is extracted with ether. The organic layers collected are dried over sodium sulphate and after removal of the solvents the residue is distilled in vacuum; a product, having a boiling-point of 70° C at 0.08 mm Hg, being obtained. This product is identical to 2-(5'-hexenyl)-5-pentyl-1-pyrroline obtained according to Example I (b).

EXAMPLE III

Biological properties of 2-(5'-n-hexenyl)-5-n-pentyl-pyrrolidine.

Under laboratory conditions amounts of $10^{-6}$ to $10^{-8}$ gms. per location yielded clear results as far as preferential experiments with Pharoah's ants are concerned in comparison with experiments without attractants. These experiments were carried out with small strips of filter paper of 10 × 0.4 cm, whether or not provided with attractive agent. Very satisfactory results were obtained with amounts of $10^{-7}$ gms. per location.

If $10^{-4}$ to $10^{-10}$ gms. of the active agent (I) were distributed as a very narrow ring with an outer circumference of 47 cm, so in an amount of 0.2 × $10^{-5}$ to 0.2 × $10^{-11}$ g/cm, worker ants as well as a a queen followed this circle for some time. The compound was spread into a ring as a solution in hexane; the hexane evaporates substantially immediately. At a laboratory experiment with an ants' population with several queens all queens present gathered after some minutes "on a cluster" on a point of the ring. This aggregating is an important phenomenon when applying the compound.

In a corresponding manner a combination of about 7 to 8 × $10^{-11}$ gms. of 2(5=-n-hexenyl)-5-n-pentyl-pyrrolidine and 2 to 3 × $10^{-11}$ gms. of 5-methyl-3-n-butyl-octahydroindolizine were distributed as a narrow ring and both workers and queens when put on this trail followed it for a longer time.

If $10^{-10}$ gms. of an attractant mixture which besides the two compounds mentioned comprises some of the homologues of both compounds in amounts of up to a few percent by weight, was distributed in a similar manner, it showed to be still more attractive to the ants, mainly due to synergistic effects of the various additional components.

We claim:

1. An attractant composition for Pharoah's ants which comprises biologically active amounts of (a) 2-(5'-n-hexenyl)-5-R-pyrrolidine wherein R is selected from the group consisting of n-pentyl, n-heptyl and n-nonyl, and (b) 5-methyl-3-n-butyloctahydroindolizine.

2. The composition according to claim 1 which comprises at least $10^{-11}$ grams of 2-(5'-n-hexenyl)-5-n-pentylpyrrolidine and at least $10^{-11}$ grams of 5-methyl-3-n-butyloctahydroindolizine.

3. The composition according to claim 2 which also comprises at least 2 × $10^{-13}$ grams of 2-(5'-n-hexenyl)-5-n-heptylpyrrolidine.

4. The composition according to claim 3 which also comprises at least 2 × $10^{-13}$ grams of 2-(5'-n-hexenyl)-5-n-nonylpyrrolidine.

5. The composition according to claim 1 which comprises about 7 to 8 × $10^{-11}$ grams of 2-(5'-n-hexenyl)-5-n-pentylpyrrolidine and about 2 to 3 × $10^{-11}$ grams of 5-methyl-3-n-butyloctahydroindolizine.

6. A method of attracting Pharoah's ants which comprises subjecting the ants to a composition having biologically active amounts effective to attract the ants of (a) a 2-(5-n-hexenyl)-4-R-pyrrolidine wherein R is selected from the group consisting of n-pentyl, n-heptyl and n-nonyl, and (b) 5-methyl-3-n-butyloctahydroindolizine.

7. The method according to claim 6 wherein the composition comprises at least $10^{-11}$ grams of 2-(5'-n-hexenyl)-5-n-pentylpyrrolidine and at least $10^{-11}$ grams of 5-methyl-3-n-butyloctahydroindolizine.

8. The method according to claim 7 wherein the composition also comprises at least 2 × $10^{-13}$ grams of 2-(5'-n-hexenyl)-5-n-heptylpyrrolidine.

9. The method according to claim 8 wherein the composition also comprises at least 2 × $10^{-13}$ grams of 2-(5'-n-hexenyl)-5-n-nonylpyrrolidine.

10. The method according to claim 9 wherein the composition comprises about 7 to 8 × $10^{-11}$ grams of 2-(5'-n-hexenyl)-5-n-pentylpyrrolidine and about 2 to 3 × $10^{-11}$ grams of 5-methyl-3-n-butyloctahydroindolizine.

* * * * *

UNITED STATES PATENT OFFICE
CERTIFICATE OF CORRECTION

Patent No. 4,075,320   Dated February 21, 1978

Inventor(s) Fridolin Jacob Ritter and Friedrich Stein

It is certified that error appears in the above-identified patent and that said Letters Patent are hereby corrected as shown below:

Col. 2, line 47, "is extremely" should read --in extremely--;
Col. 3, lines 10 and 11, "pentylpyrolidon" should read --pentylpyrrolidon--;
Col. 3, line 59, after "preparation" insert a comma;
Col. 4, line 62, delete "pentyl-1-" (2nd occurrence);
Col. 6, line 4, "2(5=-n-hexenyl)" should read --2(5'-n-hexenyl)--; and
Col. 6, line 40, "4-R-pyrrolidine" should be --5-R-pyrrolidine--.

Signed and Sealed this

Twentieth Day of June 1978

[SEAL]

Attest:

RUTH C. MASON
Attesting Officer

DONALD W. BANNER
Commissioner of Patents and Trademarks